(12) United States Patent
Alt

(10) Patent No.: US 6,217,607 B1
(45) Date of Patent: Apr. 17, 2001

(54) PREMOUNTED STENT DELIVERY SYSTEM FOR SMALL VESSELS

(75) Inventor: Eckhard Alt, Ottobrunn (DE)

(73) Assignee: Inflow Dynamics Inc., Springfield, VA (US)

( * ) Notice: Subject to any disclaimer, the term of this patent is extended or adjusted under 35 U.S.C. 154(b) by 0 days.

(21) Appl. No.: 09/366,287

(22) Filed: Aug. 2, 1999

Related U.S. Application Data

(63) Continuation-in-part of application No. 09/259,906, filed on Feb. 28, 1999, and a continuation-in-part of application No. 09/175,919, filed on Oct. 20, 1998, now Pat. No. 6,099,561.

(51) Int. Cl.$^7$ ........................................................ A61F 2/06
(52) U.S. Cl. ........................... 623/1.1; 606/192; 623/1.46
(58) Field of Search ...................... 606/192, 108, 606/194, 195, 198; 604/96; 623/1.1, 1.44, 1.46

(56) References Cited

U.S. PATENT DOCUMENTS 5,645,560 * 7/1997 Crocker et al. .................... 606/192
6,027,517 * 2/2000 Crocker et al. .................... 606/108

\* cited by examiner

Primary Examiner—Kevin Truong

(57) ABSTRACT

A stent delivery system is sized to allow it to traverse small-sized vessels of diameter in a range from about 1.25 mm to less than about 2.5 mm in a human body. The delivery system includes a balloon which has an inflated diameter less than 2.5 mm at nominal pressure and is integrated distally on a catheter for selective inflation and deflation through a lumen of the catheter. The stent is adapted to be mounted on the uninflated balloon so that the combination of the balloon when uninflated and the stent mounted thereon has a crossing profile in a range from approximately 0.5 mm to approximately 0.8 mm, to enable the delivery system to rapidly traverse the small-sized vessel for subsequent deployment of the stent at a preselected target site of the vessel. At the target site, the balloon is inflated to expand the diameter of the stent to lodge against the wall of the vessel and remain in place when the balloon is deflated and the delivery system is withdrawn from the vessel. The stent has a coating with a surface feature that increases the retention of the stent on the balloon during advancement of the stent delivery system through the vessel.

18 Claims, 1 Drawing Sheet

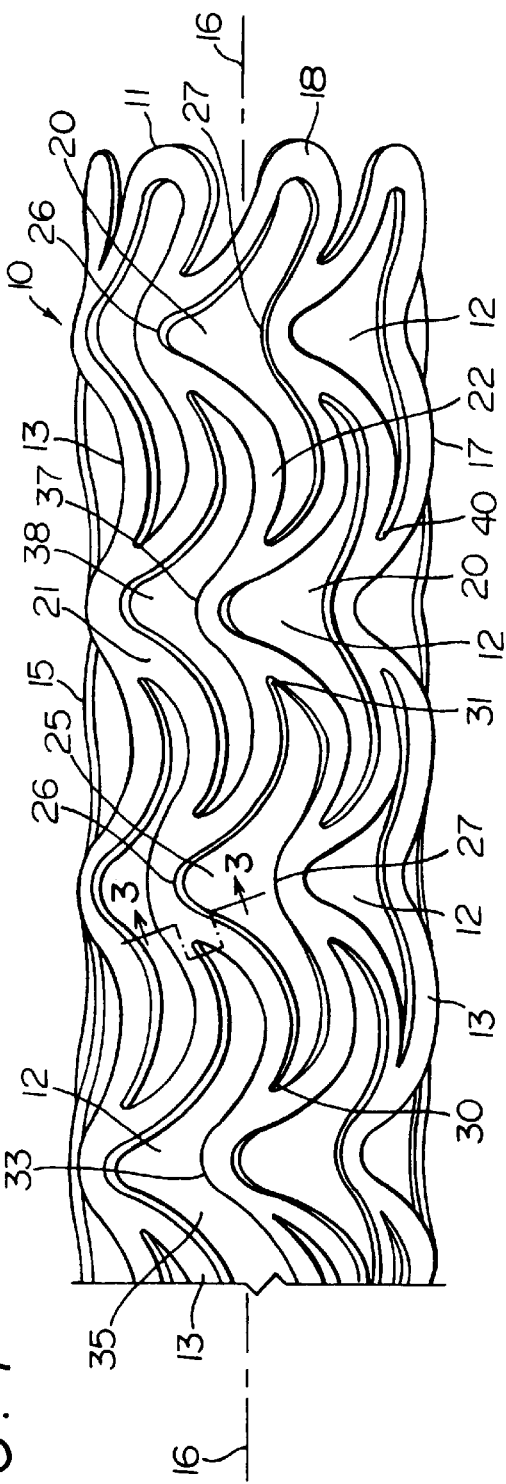
FIG. 1
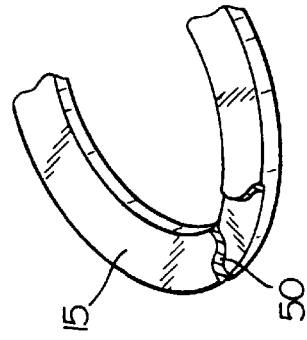
FIG. 2
FIG. 3

PREMOUNTED STENT DELIVERY SYSTEM FOR SMALL VESSELS

CROSS-REFERENCE TO RELATED APPLICATION

This application is a continuation-in-part of U.S. application Ser. No. 09/175,919, filed Oct. 20, 1998, now U.S. Pat. No. 6,099,561 and U.S. application Ser. No. 09/259,906, filed Feb. 28, 1999, now pending of the applicant herein, and is assigned to the same assignee as each of those applications.

BACKGROUND OF THE INVENTION

The present invention relates generally to stents which are implantable or deployable in a vascular or endoluminal location within the body of a patient to maintain the lumen open at that location, and more particularly to improvements in stent.

Stents are expandable prostheses employed to maintain narrow vascular and endoluminal ducts or tracts of the human body open and unoccluded, such as a portion of the lumen of a coronary artery after dilatation of the artery by balloon angioplasty. While vascular usage is frequently discussed in this application, it will be understood by those skilled in the art that stents having the characteristics and features of the present invention may be implanted in other ducts or tracts of the human body to keep the lumen open, such as in the cerebral circulation system, tracheo-bronchial system, the biliary hepatic system, the esophageal bowel system, and the urinary tract system In the case of an occluded coronary artery, for example, the original blockage is typically attributable to fatty deposits or plaque on the inner lining of the vessel. A different mechanism, however, produces a new blockage after an angioplasty procedure is performed to compress the deposits against the inner lining of the vessel, as by use of balloon angioplasty, or to virtually entirely remove the deposits, as by use of laser angioplasty or rotational cutting. The blood vessel wall is subjected to trauma by any of these procedures, which results in hyperplasia of the neointima, i.e., a rapid proliferation of muscle cells in the affected region of the wall, to cause restenosis and re-occlusion of the vessel lumen in a significant percentage of angioplasty patients within a period of from three to six months following the initial procedure.

To avoid this re-occlusion and to maintain the lumen of the vessel open, it is customary procedure to install a stent at the site in the vessel where the angioplasty was performed. The stent is deployed by radial expansion under pressure exerted by the inflating balloon of a balloon catheter on which the stent is mounted, to engage the inner lining or surface of the vessel wall with sufficient resilience to allow some contraction but also to provide a degree of stiffness to resist the natural recoil of the vessel wall following expansion.

Trends and extensions of increased knowledge and methods in practical cardiology are based primarily on advances in basic science and applied technology. For example, ten years ago, treatment of myocardial infarction (GI) stressed limiting physical injury and damage and focused principally on rehabilitation. The treatment strategy for acute MI was followed by a period of use of a thrombolytic agent. New techniques, new catheters, new stents and guidewires and improved fluoroscopic x-ray machines have more recently enabled treatment of acute MI with interventional catheter techniques. In one of these techniques, involving an angioplasty procedure, a small guidewire is advanced through an occlusion of a coronary artery which is attributable primarily to a thrombus, a balloon catheter is then advanced along the guidewire, and the balloon is inflated at the site of the thrombus to open the lumen of the artery. A stent is deployed at the lesion site either concurrently with or immediately following the angioplasty procedure to provide the necessary mechanical support to hold the lumen of the dissected vessel wall open.

This technique has been applied very successfully in coronary vessels which have a range of diameters from approximately 2.5 to 3.5 millimeters (mm). However, present day successful treatment of vessels having diameters smaller than 2.5 mm remains quite limited, because currently available apparatus and stent delivery systems are inadequate to negotiate such small vessel sizes to allow installation therein.

A wide clinical spectrum of diseases exists that would be receptive to beneficial treatment of vessels smaller than 2.5 mm in diameter. One such instance is treatment of side branches of the coronary arteries, which has a beneficial indication. A capability to treat vessels other than coronary vessels but of similarly small diameter, such as vessels enabling blood circulation in the brain, would likewise be desirable.

Ischemic stroke is characterized by pathophysiological characteristics which are very similar to those of MI. An artery is occluded either by an embolized thrombus as in patients with atrial fibrillation, or by a local thrombus that builds up on an arteriosclerotic vessel wall. Often these arteriosclerotic vessels are undergoing a local dissection, which limits the blood flow and activates the coagulation system. Access to small occluded arteries of the brain or other parts of the body for implementing procedures to allow adequate blood flow therethrough is a highly desirable objective for treating millions of persons likely to suffer stroke each year.

One of the technical prerequisites for successful treatment in these respects is the availability of a stent, and related delivery system, which is sufficiently small and thin that it can navigate and be and deployed in these tiny vessels without occluding the lumen thereof It is also essential that the stent be highly visible during and after implantation to enable proper deployment and aftercare by the physician. The latter attribute is especially important for treatment of intracerebral arteries, because of the obstacle to x-rays presented by the skull which makes precise visualization of a small thin stent extremely difficult. The stent should, therefore, be sufficiently radiopaque for valization without need for its struts to be made so large that the stent itself creates an unacceptable obstruction of the lumen of the vessel.

Another prerequisite of a successful treatment of these extremely small diameter vessels is that the stent delivery system should be highly flexible to allow it to be advanced along the anatomy of the cerebral circulation.

In addition, the total stent delivery system must be of extremely small profile, which will allow vessels of 2.0 mm, 1.75 mm or even 1.50 mm diameter to be addressed. No currently available stent delivery system has a balloon with a diameter less than about 2.5 mm when inflated at nominal pressure.

Therefore, it is a principal aim of the present invention is to provide stents and stent delivery systems having such attributes and characteristics, so as to enable successful treatment of extremely small diameter blood vessels and other ducts, tracts or conduits of the human body, without unacceptable obstruction of the vessel lumen itself.

SUMMARY OF THE INVENTION

According to the present invention, a stent and a stent delivery system are provided with features and characteristics which will allow the stent to be premounted on the balloon of the delivery system for easy introduction into and advancement through vessels having diameters in a range from about 1.25 to less than 2.5 mm. The solution to achieving these ends lies in implementing a suitably small-sized stent.

It is crucial in the case of a very small-sized stent, as with the present invention, that there be sufficient retention force between the stent and the balloon that the stent will be maintained in place on the balloon. This retention must exist throughout travel of the stent, so as to avoid having the stent dislodged from the balloon during navigation of the delivery system through the vessel. At the same time, the stent must—despite its small crossing profile which will avoid innate obstruction of the vessel lumen—possess sufficient mechanical strength to support the vessel wall at a target site where it will be deployed. Further, it must resist the natural recoil of the vessel wall which inevitably follows deployment of the stent.

Added to these prerequisites is the further need to maintain sufficient visibility of such a small-sized stent that the implanting physician is able to properly place the stent for deployment to successfully carry out the procedure.

Ordinarily, for mounting or premounting, the stent is crimped onto the balloon under external pressure. Consequently, the mesh structure of the stent undergoes considerable deformation during the crimping procedure, which takes two individual and distinct forms. First, the stent undergoes an elastic deformation in response to the external pressure applied to crimp it to a smaller diameter. In this type of deformation, the stent assumes a new shape but, because of its elastic properties, seeks to return to its former shape—even if only slightly—when the external pressure is removed. Second, the stent undergoes plastic deformation which tends to maintain the new shape that resulted from the external pressure of crimping. The greater the plastic deformation compared to the elastic deformation—i.e., the higher the ratio of the former to the latter—the higher is the retention force exerted by the stent on the balloon. As noted above, maximizing or optimizing this retention force is an important aspect of the invention.

Another important consideration in implementation of an embodiment of the present invention is the reduction of outside or exposed surface area of the balloon used in the stent delivery system, that occurs with reduction of the balloon diameter to accommodate a much smaller stent than is ordinarily encountered. For the small stent size of the present invention, the uninflated balloon diameter preferably ranges from about 0.5 to about 1.0 mm, and more preferably from about 0.5 mm to about 0.8 mm. The resultant relatively small outside surface area of the balloon has a further deleterious effect on retention force exerted by the stent when mounted in crimped fashion on the balloon.

Therefore, it is another important aim of the present invention to provide a premounted stent delivery system suitable for traversing body vessels, ducts or tracts having lumen diameters in a range from about 1.25 mm to less than about 2.5 mm, in which the stent exhibits a very high retention force despite the small diameter of the stent and the delivery system balloon and the relatively small outer surface area of the balloon.

According to the invention, the stent is provided with a rough surface characteristic, rather than a smooth surface as is typical for stents, and this rough surface characteristic or feature significantly increases the retention force of the stent on the balloon. A coating material is applied whose inherent material characteristics serve to increase the surface structure and area of the basic stent to which it is applied or on which it is formed. Such a surface characteristic is provided, for example, by the techniques and methods described in co-pending U.S. patent applications Ser. No. 09/059,053 and Ser. No. 09/175,919 of the applicant herein, assigned to the same assignee as the present application. The finished stent has a multi-layer surface region, the outer layer being a ceramic-like material with a relatively rough external surface. This outer layer is biocompatible and may be very thin, with the composition of a compound or derivative of certain metals such as iridium oxide (sometimes referred to herein as "IROX") or titanium nitrate. The outer layer overlies the entire exposed surface of the stent, so that when the stent is mounted on and crimped against the balloon of the stent delivery system, the rough surface structure of the stent lumen resides directly against the outer surface of the balloon along the area of contact. The surface roughness, however, is not so extreme as to potentially puncture the balloon. Creation of a rough surface may be achieved by a number of alternative techniques, beyond those disclosed in the aforementioned '053 and '919 applications, examples of which will be described in the detailed description below.

In a preferred embodiment, the multi-layer stent is composed of three different layers including an innermost tubular core, an intermediate corrosion-resistant layer overlying the core material, and the aforementioned thin ceramic-like metal or derivative thereof outer layer overlying the intermediate layer and providing the rough surface characteristic of the overall stent. In an exemplary embodiment, the core material is medical grade stainless steel, the intermediate layer is gold, and the outer layer is IROX. It is important that each of the intermediate and outer layers tightly adhere to its respective directly underlying layer material. Tight adherence of the gold coating to the underlying steel core may be achieved, for example, by a process described in U.S. Pat. No. 5,824,045, which is assigned to the assignee of the present application. The noble metal layer (e.g., gold) aids both in keeping the total thickness of the stent relatively small, while considerably enhancing the visibility of the stent on x-ray fluoroscopy over the visibility of a correspondingly thin layer of steel, for example, to aid the implanting physician in guiding the stent to and deploying it at a desired target site in the vessel.

The core material of the stent is generally constructed of an elongate biocompatible metal member composed, for example, of 316L stainless steel (medical grade), but may alternatively be composed of other biocompatible material such as titanium, Nitinol (nickel-titanium alloy with shape memory characteristics), iridium, or other metal, which is configured in an open-ended tubular or cylindrical shape (e.g., coil, mesh, undulating single wire filament or perforated tube). For convenience, the portion of the stent between its open ends is referred to herein as the sidewall, regardless of the particular tubular shape of the structure, and as having openings therethrough even though a coil stent has only one continuous spiral opening in its sidewall and a continuous filament wire may have very large openings in its "sidewall."

When mounted on the balloon, the stent of the present invention is of sufficiently small diameter—with a total crossing profile of from 0.5 to 0.8 mm, depending on final size—to be accommodated by and to readily traverse a vessel, tract or other duct of patient's body less than 2.5 mm in diameter, and optimally between 1.25 mm and 2.5 mm, to the site at which the stent is to be deployed. The rough outer surface of the stent serves to increase the retention force of the stent when crimped on the balloon, for secure retention of the stent and ease of navigation of the stent delivery system through the vessel. Deployment is achieved by controlled inflation of the balloon of the stent delivery system to apply a uniform radial outwardly directed force on the sidewall of the stent to increase its diameter, and thereby expand or open the stent until it is in firm contact or engagement with the inner lining of the vessel wall, for retention at that site. The mechanical strength of the stent should be adequate to resist collapse from the natural recoil of the vessel wall when the balloon is deflated and the delivery system is withdrawn from the patient's body.

Thus, despite a smaller area of contact between the stent and the balloon of the delivery system, a high retention force is created as a consequence of the increased friction between them owing to the relatively rough surface of the stent. There is no need for taking special pains for fitting or aligning components or for increasing the diameter (which could defeat the desire to navigate the small-sized vessels), and even balloons that are normally used solely for balloon angioplasty will suffice for use as the balloon of the stent delivery system.

Another problem typically encountered in stent delivery systems sought to be used in small-sized vessels is that the sidewall thickness of the stent has been made relatively large in an effort to achieve improved retention force on the balloon. But a large wall thickness undesirably reduces the lumen diameter of the vessel at the site of deployment of the stent. For to example, in a vessel of 1.50 mm lumen diameter, a stent with a wall thickness of 0.125 mm results in a lumen diameter reduction of 0.25 mm, i.e., a loss of almost 17% in total lumen diameter. In the stent delivery system and method of the present invention it is possible to use a stent having a wall thickness of much smaller dimension—in a range on the order of only 50 microns (micrometers, or $\mu$m) to 75 $\mu$m—and thereby, with considerably less adverse effect on vessel lumen diameter. This is because the increased friction attributable to the rough surface of the stent compensates for the lower retention force attributable to the reduced sidewall thickness of the stent.

BRIEF DESCRIPTION OF THE DRAWINGS

The above and still further aims, objectives, features, aspects and attendant advantages of the present invention will become apparent from the following detailed description of preferred embodiments and methods of manufacture and usage of a stent and a delivery system on which the stent is premounted, constituting the best mode presently contemplated of practicing the invention, when taken in conjunction with the accompanying drawings, in which:

FIGS. 1 and 2 are, respectively, a perspective view of an embodiment of a vascular or endoluminal stent having a rough surface structure according to the present invention, and a relatively enlarged partially-processed fragmentary portion thereof; and FIG. 3 is a cross-sectional view of a three-layer preferred embodiment of the stent of FIG. 1.

DETAILED DESCRIPTION OF PREFERRED EMBODIMENT AND METHOD

Each of the '919 and '906 applications is incorporated in its entirety into this specification by reference. Nevertheless, for the sake of convenience to the reader, certain portions of the two co-pending applications will be repeated in some detail herein.

In FIG. 1 (not to scale) stent 10 is fabricated as a hollow tubular self-supporting structure or member 11 composed of a biocompatible metal such as medical grade 316L stainless steel, although other metals may alternatively be used, such as titanium, iridium, or Nitinol, for example. The tubular member is provided with a multiplicity of through-holes or openings 12 through sidewall 15, defined and bounded by a plurality of struts or links 13, which enables expansion of the stent diameter when the device is to be deployed at a target site in a vessel, duct or tract of the human body. The openings 12 may be precisely cut out to form a latticework sidewall using, for example, a narrow laser beam following a programmable pattern. The removed material is discarded.

By way of example, the resulting pattern in the latticework sidewall 15 is a network of interconnected struts 13 which are optimized for orientation predominantly parallel to the longitudinal axis 16 of the tube 11, with none of the struts oriented perpendicular (i.e., transverse) to the axis 16, so that no strut interconnecting any other struts in the latticework is oriented to lie completely in a plane transverse to the longitudinal axis, without running from one end of the stent to the opposite end. This structure, described in detail in applicant's copending application Ser. No. 08/933,627, also incorporated by reference in its entirety herein, provides a very low friction characteristic (or coefficient of friction) of the outer surface 17 of the stent, to ease advancement of stent 10 in a vessel, duct or tract to a site for deployment.

The network or latticework of struts 13 defines a series of longitudinally repeating circumferential rows of openings 12. Each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof When the stent 10 is crimped onto a small diameter (low profile) delivery balloon (not shown), the adjacent circumferentially aligned crests of each row move closer together, and the pattern formed by the latticework of struts allows substantial nesting together of the crests and bows, which assures a relatively small circumference of the stent in the crimped condition. This stent is highly flexible, and is capable of undergoing bending to a small radius corresponding to radii of particularly tortuous coronary arteries, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. It bears emphasis, however, that the configuration of this stent structure, while highly desirable, is illustrative only and not essential to the principles of the present invention.

The tubular steel core sidewall 15 of the stent is coated with a thin, tightly adherent layer 50 (FIG. 2, a fragmentary perspective view shown partly in section for clarity) of noble metal, preferably gold, but alternatively an alloy which is primarily composed of gold or other noble metal. The gold layer is applied to cover the entire exposed surface of the basic metal stent, whether of the type shown, or a metal mesh, or other configuration. This is preferably but not necessarily achieved by a method described in the aforementioned '045 patent, which is incorporated in its entirety herein by reference. Preferably, this layer has a thickness in a range from 1 $\mu$m to 10 $\mu$m, and more preferably about 5 $\mu$m.

According to the latter patent, the thin adherent film or layer 50 of gold is applied by a process of ion beam deposition to provide a firm, tightly bonded, extremely thin foundation layer, which allows the bond between base metal and noble metal to flex without suffering fracture or peeling of the overlying layer. This initial foundation layer is built upon preferably by a conventional galvanic process by which one or more additional thin, tightly adherent uniform layers of gold are applied, to form an overall composite layer of gold having a thickness of from about 3 $\mu$m to about 6 $\mu$m, and preferably about 5 $\mu$m, on each side of the wall of the stent. The overall effect of these processes is a layer adherence that precludes cracking, peeling or flaking of any portion of the overall gold layer from the underlying surface of the steel core, which might otherwise occur during times when the stent is undergoing mechanical stress and distortion, such as during pre-opening, crimping, and expansion-during deployment phases of the procedure.

Stent 10 preferably is composed of three different primary or fundamental layers as shown in the greatly exaggerated fragmentary cross-sectional view of FIG. 3, taken through the line 3—3 of FIG. 1. By "primary" and "fundamental", as used here, it is meant that although the stent may have additional layers, coatings or films, the three layers—two of which have been described thus far—are important to the favorable characteristics enjoyed by the stent.

The third or upper or outermost layer 80 is preferably composed of a ceramic-like metal material such as either iridium oxide (IROX) or titanium nitrate, these materials being exemplary of a biocompatible layer that serves a primary purpose of avoiding tissue irritation and thrombus formation. This outermost layer may be deposited as an inert coating over the surface(s) of the underlying intermediate noble metal layer by any known method, preferably to a thickness in the range from about 500 nm to about 1,500 nm (=1.5 $\mu$m). This outermost layer is also preferably applied to all exposed surfaces of the wall of stent 10, so it is the surface that contacts both the inner lining of the vessel and the blood flowing through the lumen of the vessel in which the stent is implanted (deployed).

In addition to assuring the absence of a galvanic potential that could cause corrosion of the base layer, the intermediate noble metal layer serves to enable flexing of the stent over a vast number of cycles encountered in actual use without loss of the overlying rough surface coating (outermost layer) from flaking, shedding or disintegration.

A high voltage sputtering process is among many suitable processes that may be used to form this outermost rough surface coating. Others include anionic oxidation, thermal oxidation, sintering, and electrodeposition. Oxalic acid, application of current and heat, and additional use of an ultrasound bath have been found to produce a very tight adhesion of iridium oxide to the underlying intermediate layer. Suitable processes for forming iridium oxide or titanium nitrate layers also have been developed and can be performed by Hittman Materials & Medical Components, Inc. of Columbia, Md., for example. In any event, the outermost layer 80 is formed with a relatively rough surface, for purposes of providing the increased friction factor and retention force according to the present invention.

A three layer stent structure can be produced with an overall thickness in a range from about 50 $\mu$m to about 75 $\mu$m. The stainless steel wall may be fabricated in a thickness of approximately 45 to 60 $\mu$m, which offers sufficient mechanical strength to resist the natural recoil of the blood vessel wall following deployment of the stent. The gold intermediate layer is applied in a 5 $\mu$m thickness, for example, to all exposed surfaces of the base layer, giving a total additional thickness of about 10 $\mu$m to the structure, and serving to avoid a galvanic potential. The outermost layer of iridium oxide is formed to a thickness preferably in a range from 500 nanometers (nm) to about 1.0 $\mu$m.

The most preferred method of producing the outermost stent coating of iridium oxide is described in detail in the '906 application. Briefly, the method employs a combination of a chemical bath process together with application of heat and mechanical forces. An ultrasonic water bath is maintained at a preselected water temperature according to the setting of a thermostat. Initially, the surface of each stent to be coated is prepared by activation. For a gold-coated stent with a base or core metal of medical grade stainless steel, iridium, titanium or Nitinol, for example, adequate surface activation is achieved by immersing the stent in a solution of 10% oxalic acid at a temperature of about 100° C., for a period of about 30 minutes. The stents are then thoroughly rinsed with distilled water and dried in air at a laminar flow at room temperature. Each stent is then inserted into a respective glass vial for the coating process, and the vials are then inserted into respective holders of a tray or trays for partial submergence in the water bath.

A quantity of coating solution is added to the vial sufficient to cover the stent. The coating solution is prepared by dissolving 200 milligrams (mg) of iridium chloride in 5 ml of 20% hydrochloric acid, in a separate reaction beaker, then boiling slowly at approximately 100° C. until the solution is evaporated to approximately 20% of its original volume, e.g., from 5 ml to one ml. Although the coating solution may be stored, it is preferably used within seven days after having been prepared. 500 microliters ($\mu$l) of coating solution was found to be sufficient for full coverage of the stent for a vial with a liquid content capacity of one milliliter (ml), but the amount of coating solution to be added to a vial for a particular stent will depend on and be adjusted according to the size and surface dimensions of the stent to be coated. Each vial is closed with a stopper having a tiny hole for pressure relief during operation of the bath.

In the bath, the vials are arranged in the holder such that each is upright and the entire stent lies completely below the bath water level. In an exemplary operation of the bath, the ultrasonic generator delivered a mean energy of 320 watts at a frequency of 35 kiloHertz (kHz). The vials and stents undergo vibration at that frequency, and the water bath undergoes heating up to the preset temperature, which is maintained by virtue of circulating coolant water at the exterior of the bath, while continuously maintaining the ultrasonic vibrational energy for adherence of the coating.

During the ultrasonic bath operation, the iridium chloride in the coating solution substantially uniformly coats the submerged stent with a layer of iridium chloride, which is ultimately converted to iridium oxide during retention of the vials in the bath in the presence of heat, ultrasonic energy, and air. Any molecular bound water leaves the crystal structure of the iridium oxide following the heating.

After a period of time—at least about 6 hours of bath operation in an exemplary procedure—the vials are removed from the bath, and the stents are then removed from the vials, rinsed with de-ionized pure water, and dried in a laminar flow of air for about one hour at room temperature. This is followed by heating the coated stents in an oven for about 12 hours at a temperature of 320° C. The heating converts any residual iridium chloride in the coating to iridium oxide, so as to create the final complete iridium oxide coating. Then the stents are cleaned ultrasonically and with alcohol in a manner which is customary for biomedical implants.

Stents averaging 16 mm in length, with a diameter suitable for mounting on an uninflated balloon of a diameter from about 0.5 to 1.0 mm and a strut thickness of from about 50 to 75 $\mu$m underwent a slight increase in weight which depended on the desired coating thickness. A coating thickness ranging from about 500 nm to about 1 micron maybe optimum.

Tests conducted on stents coated by this method including vibrational, ultrasonic, bench and maximum expansion/repeated crimping tests—have demonstrated that the iridium oxide is firmly attached to the underlying base or core metal of the stent, so this outer layer will neither flake off nor disintegrate from the stent even with maximum expansion during subsequent implantation and deployment. It is believed that by the continuous application of ultrasonic energy in the coating method, only those iridium oxide molecules that attach to the underlying base metal enter into a very firm bond, while the other molecules are removed from the stent and, with the ultrasonic induced vibration, are dissolved in the prepared solution.

The thickness of the iridium oxide layer which is formed on the base metal of the stent, and the roughness of its exposed surface, are controlled by appropriate variation of the iridium compound and its amount and concentration in the prepared solution, as well as by the characteristics of the ultrasonic bath. A relatively rough outer surface on the firmly bonded iridium oxide layer, and thus of the overall stent itself provides numerous indentations.

The rough outer surface serves to increase the coefficient of function and the retention force of the stent when mounted on a balloon for implantation in a small-sized vessel of the human body. A considerable risk exists that a balloon catheter-mounted stent might be dislodged from the uninflated or partially inflated balloon as a result of navigation through the tortuous path of the cardiovascular system or other vessels of the body to the preselected site for deployment, particularly if the stent surface is smooth and/or the stent thickness and diameter are small. The rough surface of the outer layer provides the stent with high retention force, exceeding 2.5 Newton, even where less mechanical grip exists because of thin stent strut thickness, and the stent is mounted on a small diameter (e.g., <1.0 mm, uninflated) balloon.

Other techniques may alternatively be used for forming a relatively rough outer surface on the stent, suitable for purposes of the present invention. For example, the surface may be treated to electropolishing in which an acid is applied or added to the bath, and a predetermined current of several amperes is applied, so as to create a rough rather than a smooth surface. Or, metal particles may be sputtered onto the metal surface of the stent, such as stainless steel 316L particles sputtered onto a 316L stent surface, to increase the surface roughness. Or, the stent may be cut from a rough and porous tubing using techniques which have been implemented by the aforementioned Hittman company. These examples are merely illustrative, not exhaustive.

Although the iridium oxide coating on the stent is an inorganic biomaterial, it exhibits an ability to reduce the degree of inflammation which could otherwise occur when such biomaterial contacts the human body. Normally, an inorganic biomaterial is a passive structure with only passive mechanical properties. But it has been found that iridium oxide produced by the preferred method herein has catalytic properties, capable of promoting a reaction in which hydrogen peroxide ($H_2O_2$) is converted into water ($H_2O$) and oxygen ($O_2$). This reaction normally occurs only in the presence of a catalyst, since hydrogen peroxide is normally kinetically stable and will not decompose spontaneously. To become unstable, a certain kinetic energy is required to overcome the activation energy for hydrogen peroxide decomposition.

It is known that one of the very first responses of the human body to the implantation of a foreign body, such as a stent surface, into the blood vessels is the activation of leukocytes, white blood cells which are one of the formed elements of the circulating blood system. This activation causes oxidative stress with a burst of reactive oxygen compounds (100 times higher than the baseline production). One of the key molecules in this process is hydrogen peroxide, released by neutrophilic granulocytes which constitute one of the five types of leukocytes. While $O_2$ is always present and generated in a normal cell cycle, in the mitochondria the reaction of $O_2$ to superoxide anion $O_2$ (i.e., reactive form of oxygen when molecular oxygen gains a single electron) is reduced to $H_2O_2$ by the enzyme superoxide dismutase. The enzyme catalase serves as a converter of $H_2O_2$. The presence of $H_2O_2$ is a very strong trigger for inflammation. And in a situation where inflammation is occurring, when the granulocytes produce 100 times more $O_2$ than normal, the normal catalytic activity of the body is insufficient to convert the increased amount of $H_2O_2$ to water and oxygen in its metabolic process. It has been found that this iridium oxide surface of the stent, though a primarily passive structure, is a biologically active surface which is highly effective in preventing inflammatory reactions. The presence of catalytic properties of an otherwise biologically inactive surface of this biomaterial appears to be partly attributable to molecular adherence of the iridium structure as discussed above, and partly attributable to the porous surface structure of the iridium oxide layer, which enables the stent to be implanted without significant inflammation.

It will be observed that the stent delivery system, method of assembly, and stent of the present invention provides sizing to allow the stent delivery system to traverse small-sized vessels of a human body, nominally ranging in diameter from about 1.25 to less than about 2.5 mm. The delivery balloon has an uninflated diameter considerably less than 2.5 mm, and indeed less than 1.0 mm, ideally from about 0.5 to 0.8 mm, integral with the catheter distally thereof i.e., at or near the distal end of the catheter, through which the balloon may be selectively inflated and deflated via an inflation lumen of the catheter. The stent is adapted to be firmly but removably mounted on the uninflated balloon, as by crimping thereon, and typically is premounted in that way for use by the implanting surgeon upon removal of the delivery system from its package. The overall diameter of this assembly and its crossing profile preferably lies in a range from about 0.5 mm to about 0.8 mm. One of the stent and the balloon includes a feature for increasing the retention force between the stent and the balloon while the stent is mounted on the balloon, so that the stent is held securely in place as the stent delivery system is navigated through the vessel.

According to the preferred embodiment, that is the function of the stent's outer rough surface. It is also possible, however, albeit not preferable, within the confines of the invention, to provide a surface feature of the balloon to achieve that end, or to apply a medical grade biodegradable biomaterial adhesive to the portion of the balloon surface on which the stent is to be mounted. But an adhesive may prevent release of the balloon after the stent is deployed.

Although certain methods and embodiments of the invention have been disclosed herein, it will be recognized from a consideration of the foregoing description that variations and modifications may be made without departing from the spirit and scope of the invention. Accordingly, it is intended that the invention shall be limited only by the appended claims and the rules and principles of applicable law.

What is claimed is:

1. A small profile stent delivery system for traversing small vessels of less than about 2.5 mm diameter of a human body, comprising a catheter having a balloon integrated distally on said catheter for selective inflation and deflation via an inflation lumen of said catheter; a stent firmly mounted on said balloon for traversal of a said small vessel by the delivery system and subsequent deployment of said stent at a preselected target site of the vessel by inflation of said balloon to expand the diameter of said stent to lodge against the inner wall of the vessel; said balloon having an optimum inflated diameter less than about 2.5 mm at nominal balloon pressure of from about 6 atmospheres (atm) to about 8 atm; one of said balloon and said stent having a non-adhesive intrinsic surface region characteristic implemented to enhance the retention force between said balloon and said stent mounted thereon to prevent said stent from being dislodged from said balloon as the delivery system traverses a said small vessel despite the small profile of the delivery system but to permit said stent to be released from said balloon and remain lodged against the inner wall of the vessel after deployment at the target site and deflation of said balloon and removal of said catheter from the vessel.

2. The small profile stent delivery system of claim 1, wherein said balloon when substantially uninflated with said stent mounted thereon for traversal of a said small vessel, together have an overall diameter and crossing profile in a range from approximately 0.5 mm to approximately 0.8 mm.

3. The small profile stent delivery system of claim 1, wherein said non-adhesive intrinsic surface region characteristic substantially increases the friction between said balloon and said stent mounted thereon relative to an absence of said characteristic.

4. The small profile stent delivery system of claim 3, wherein said non-adhesive intrinsic surface region characteristic comprises a rough surface of said stent along at least the surface of said stent in contact with said balloon when said stent is mounted on said balloon.

5. The small profile stent delivery system of claim 4, wherein said rough surface of said stent comprises a layer of ceramic-like material adherently overlying the entire surface of said stent.

6. The small profile stent delivery system of claim 4, wherein said rough surface of said stent comprises a layer of material selected from a group consisting of iridium oxide and titanium nitrate adherently overlying the entire surface of said stent.

7. The small profile stent delivery system of claim 6, wherein said stent has a total sidewall thickness in a range from about 50 $\mu$m to about 75 $\mu$m.

8. The small profile stent delivery system of claim 6, wherein said delivery system has a crossing profile sized to traverse vessels having a lumen diameter in a range from about 1.5 mm to less than 2.5 mm.

9. A method of assembling a small profile stent delivery system for traversing small-sized vessels of less than 2.5 mm diameter in a human body, comprising the steps of selecting a balloon catheter with an integral distal balloon having an optimum inflated diameter less than 2.5 mm at nominal balloon pressure of from about 6 atmospheres (atm) to about 8 atm wherein said balloon is selectively inflatable and deflatable through an inflation lumen of said catheter; mounting firmly on said balloon a stent having a non-adhesive intrinsic surface region characteristic along its surface adapted to reside against the surface of said balloon to enhance the frictional force and thereby the retention force between said balloon and said stent mounted thereon whereby the combination of said balloon when uninflated and said stent mounted thereon has an overall diameter and crossing profile in a range from approximately 0.5 mm to approximately 0.8 mm and said stent delivery system is equipped to traverse a said small-sized vessel without dislodging said stent from said balloon during advancement to a preselected target site and to freely release said stent from said balloon upon deployment of said stent against the vessel wall at said target site and deflation and withdrawal of said balloon from the small-sized vessel.

10. The method of claim 9, including the step of forming said non-adhesive intrinsic surface region characteristic of said stent by roughening the surface of said stent at least along an area adapted to contact said balloon.

11. The method of claim 10, wherein said roughening step includes forming an adherent surface layer comprising a ceramic-like material overlying said stent.

12. The method of claim 10, wherein said roughening step includes forming an adherent surface layer of a material selected from a group consisting of iridium oxide and titanium nitrate overlying said stent.

13. The method of claim 12, including selecting said stent to have a sidewall thickness in a range from about 50 $\mu$m to about 75 $\mu$m after said surface layer is formed thereon.

14. A small profile stent delivery system adapted to traverse a vessel of less than 2.5 mm diameter in a human body, said stent delivery system including a catheter, a balloon having an inflated diameter less than about 2.5 mm at nominal pressure between about 6 and 8 atm integrated distally on said catheter for selective inflation and deflation through an inflation lumen of said catheter, a stent mounted on said balloon, said stent comprising an expandable diameter metal tube, the combination of said balloon when uninflated and said stent mounted thereon having a crossing profile in a range from approximately 0.5 mm to approximately 0.8 mm, said stent having a coating overlying an exposed surface thereof adapted to reside in contact with said balloon when said stent is mounted thereon, said coating including material to enhance fluoroscopic visibility of said stent and to create a rough region along said exposed surface to increase the retention force between said stent and said balloon.

15. The small profile stent delivery system of claim 14, wherein said coating is devoid of adhesives.

16. The small profile stent delivery system of claim 14, wherein said coating comprises a ceramic-like material.

17. The small profile stent delivery system of claim 16, wherein said ceramic-like material is selected from a group consisting of iridium oxide and titanium oxide.

18. The small profile stent delivery system of claim 14, wherein said stent sidewall has a total thickness in a range from about 50 μm to about 75 μm.

* * * * *